(12) United States Patent
Hamamoto

(10) Patent No.: US 10,543,347 B2
(45) Date of Patent: Jan. 28, 2020

(54) DELIVERY SYSTEM FOR PERCUTANEOUS ABSORPTION DRUG PREPARATION AND METHOD FOR MANUFACTURING SAME

(71) Applicant: MEDRX CO., LTD., Higashikagawa-shi, Kagawa (JP)

(72) Inventor: Hidetoshi Hamamoto, Higashikagawa (JP)

(73) Assignee: Medrx Co., Ltd., Higashikagawa-shi, Kagawa (JP)

( * ) Notice: Subject to any disclaimer, the term of this patent is extended or adjusted under 35 U.S.C. 154(b) by 0 days.

(21) Appl. No.: 15/552,742

(22) PCT Filed: Feb. 23, 2016

(86) PCT No.: PCT/JP2016/055246
§ 371 (c)(1),
(2) Date: Aug. 22, 2017

(87) PCT Pub. No.: WO2016/136732
PCT Pub. Date: Sep. 1, 2016

(65) Prior Publication Data
US 2018/0028796 A1  Feb. 1, 2018

(30) Foreign Application Priority Data

Feb. 24, 2015 (JP) .................. 2015-033806

(51) Int. Cl.
*A61K 9/00* (2006.01)
*A61M 35/00* (2006.01)
(Continued)

(52) U.S. Cl.
CPC .......... *A61M 35/00* (2013.01); *A61K 9/7007* (2013.01); *B32B 7/06* (2013.01); *B32B 7/12* (2013.01);
(Continued)

(58) Field of Classification Search
CPC ................................................... A61K 9/7007
See application file for complete search history.

(56) References Cited

U.S. PATENT DOCUMENTS

| 5,820,877 A | 10/1998 | Yamaguchi et al. |
| 5,993,852 A | 11/1999 | Foldvari et al. |

(Continued)

FOREIGN PATENT DOCUMENTS

| JP | 2001-514212 A | 9/2001 |
| JP | 3973420 B2 | 9/2007 |

(Continued)

OTHER PUBLICATIONS

International Search Report (PCT/ISA/210) dated May 10, 2016, by the Japanese Patent Office as the International Searching Authority for International Application No. PCT/JP2016/055246.

(Continued)

*Primary Examiner* — Benjamin J Packard
(74) *Attorney, Agent, or Firm* — Buchanan Ingersoll & Rooney PC

(57) ABSTRACT

Provided is a novel delivery system for a percutaneous absorption drug preparation. The delivery system for a percutaneous absorption drug preparation is provided with: a solvent-impermeable first sheet; a solvent-impermeable second sheet that is bonded to the top surface of the first sheet and comprises a non-sealed area and a sealed area surrounding the non-sealed area, said non-sealed area and sealed area being formed between the first sheet and the second sheet, and a cutting part circularly extending along the outer peripheral edge of the non-sealed area; a percutaneous absorption drug preparation-holding member that is disposed between the first sheet and the second sheet in the non-sealed area and fixed to the second sheet inside the cutting part; and a pressure-sensitive adhesive third sheet (Continued)

that is removably bonded to the top surface of the second sheet.

8 Claims, 3 Drawing Sheets

(51) Int. Cl.
    *A61K 9/70*     (2006.01)
    *B32B 7/06*     (2019.01)
    *B32B 7/12*     (2006.01)

(52) U.S. Cl.
    CPC ...... *A61M 2207/00* (2013.01); *B32B 2535/00* (2013.01)

(56) References Cited

U.S. PATENT DOCUMENTS

| | | | |
|---|---|---|---|
| 6,104,950 | A | 8/2000 | Higo et al. |
| 2008/0172015 | A1 | 7/2008 | Okada et al. |
| 2009/0011159 | A1 | 1/2009 | Okada et al. |

FOREIGN PATENT DOCUMENTS

| | | | |
|---|---|---|---|
| JP | 4262934 | B2 | 5/2009 |
| JP | 4335317 | B2 | 9/2009 |
| JP | 4879442 | B2 | 2/2012 |
| JP | 4975534 | B2 | 7/2012 |
| JP | 5059584 | B2 | 10/2012 |
| WO | WO 95/16440 | A1 | 6/1995 |
| WO | WO 97/06847 | A1 | 2/1997 |
| WO | WO 98/13000 | A1 | 4/1998 |
| WO | WO 99/11247 | A1 | 3/1999 |
| WO | WO 01/91848 | A2 | 12/2001 |
| WO | 2007067363 | A2 | 6/2007 |

OTHER PUBLICATIONS

Written Opinion (PCT/ISA/237) dated May 10, 2016, by the Japanese Patent Office as the International Searching Authority for International Application No. PCT/JP2016/055246.

English language translation of International Preliminary Report on Patentability (Forms PCT/IB/338, PCT/IB/373 and PCT/ISA/237), with Written Opinion, dated Sep. 8, 2017, by the International Bureau of WIPO in corresponding International Application No. PCT/JP2016/055246. (8 pages).

Extended European Search Report issued in corresponding European Patent Application No. 16755476, dated Sep. 27, 2018 (7 pages).

DELIVERY SYSTEM FOR PERCUTANEOUS ABSORPTION DRUG PREPARATION AND METHOD FOR MANUFACTURING SAME

TECHNICAL FIELD

The present invention relates to a delivery system for a percutaneous absorption drug preparation and a method for manufacturing the same.

BACKGROUND ART

Conventionally, there has been known a delivery system for a percutaneous absorption drug preparation, which retains, with an aid of an adhesive sheet, a percutaneous absorption drug preparation carrying member carrying a material having a medicinal ingredient for a percutaneous absorption drug preparation on the skin.

For example, Patent Document 1 discloses a wound dressing. The wound dressing includes a backing material, a pressure-sensitive adhesive layer coating a portion of the backing material, an absorbent web affixed to the backing material by an adhesive means and providing voids to an exudate from a wound, and the pressure-sensitive adhesive layer contains an antibacterial agent restraining microorganisms from entering the web from the external environment.

Patent Document 2 discloses an iontophoresis delivery system for a drug. This system includes a backing (closure) having a recess, a drug-absorbent substance stored in the recess, a web bonded in a peelable manner to the backing to cover the recess, and a reservoir attached to an inner surface of the web such that a drug aliquot absorbed in the drug-absorbent substance is absorbed in a patient contact surface.

Patent Document 3 discloses a wound covering material covering and protecting a wound surface of the body. This wound covering material comprises an adhesive supporting material made up of a film or a nonwoven fabric etc., an adhesive layer disposed on one surface of the adhesive supporting material, and a hydrous gel layer, and the hydrous gel layer is affixed to the adhesive layer.

Other delivery systems for percutaneous absorption drug preparations having similar configurations are also proposed in Patent Documents 4 to 6.

PRIOR ART DOCUMENTS

Patent Documents

Patent Document 1: JP 4335317 B
Patent Document 2: JP 4879442 B
Patent Document 3: JP 3973420 B
Patent Document 4: JP 4262934 B
Patent Document 5: JP 5059584 B
Patent Document 6: JP 4975534 B

SUMMARY OF THE INVENTION

Problem to be Solved by the Invention

It is an object of the present invention to provide a novel delivery system for a percutaneous absorption drug preparation and a method for manufacturing the same, the system being different in configuration from the above-described delivery systems for percutaneous absorption drug preparations.

Means for Solving Problem

A delivery system for a percutaneous absorption drug preparation according to an embodiment of the present invention comprises
  (a) a solvent-impermeable first sheet;
  (b) a solvent-impermeable second sheet affixed to an upper surface of the first sheet, forming a non-sealing region and a sealing region surrounding the non-seal region with the first sheet, and having a cutting part formed to annularly extend along an outer circumferential edge of the non-sealing region;
  (c) a percutaneous absorption drug preparation carrying member disposed between the first sheet and the second sheet in the non-sealing region and fixed to the second sheet inside the cutting part; and
  (d) a third sheet affixed in a peelable manner to an upper surface of the second sheet.

A delivery system for a percutaneous absorption drug preparation according to an embodiment of the present invention comprises
  (a) a backing sheet having a base material layer and an adhesive layer disposed on a lower surface of the base material layer;
  (b) a solvent-impermeable base sheet affixed in a peelable manner to a lower surface of the adhesive layer and having an annular cutting part, an inner region located inside the annular cutting part, and an outer region located outside the annular cutting part;
  (c) a percutaneous absorption drug preparation carrying member fixed to the base sheet in the inner region of the base sheet; and
  (d) a solvent-impermeable cover sheet disposed on a lower surface of the base sheet to cover at least the inner region, fixed to the base sheet in the outer region of the base sheet, and continuously sealing the circumference of the inner region,
  (e) the device allowing the outer region of the base sheet to be peeled off along with the cover sheet fixed to the outer region while leaving the inner region of the base sheet on the backing sheet along with the percutaneous absorption drug preparation carrying member.

A method for manufacturing a delivery system for a percutaneous absorption drug preparation according to an embodiment of the present invention comprises
  a step 1 of supplying a solvent-impermeable base sheet including an outer region and an inner region surrounded by the outer region;
  a step 2 of forming an annular cutting part in the base sheet along an outer circumferential edge of the inner region;
  a step 3 of disposing a percutaneous absorption drug preparation carrying member in the inner region on a lower surface of the base sheet;
  a step 4 of fixing the percutaneous absorption drug preparation carrying member to the base sheet;
  a step 5 of allowing the percutaneous absorption drug preparation carrying member to carry a drug preparation;
  a step 6 of disposing a solvent-impermeable cover sheet on the lower surface of the base sheet to cover the percutaneous absorption drug preparation carrying member carrying the drug preparation;
  a step 7 of fixing the cover sheet to the base sheet and sealing the circumference of the inner region in the outer region; and
  a step 8 of affixing a backing sheet in a peelable manner to an upper surface of the base sheet.

Effect of the Invention

According to the delivery system for a percutaneous absorption drug preparation of the present invention and the delivery system for a percutaneous absorption drug preparation manufactured by the method for manufacturing of the present invention, the cover sheet (first sheet) is peeled off when used. At this time, the base sheet (second sheet) is broken at the cutting part, and the outer region of the base sheet is peeled off along with the cover sheet while the inner region of the base sheet (second sheet) is left on the backing sheet along with the percutaneous absorption drug preparation carrying member. Therefore, the percutaneous absorption drug preparation carrying member does not peel off regardless of which direction the delivery system for a percutaneous absorption drug preparation is oriented in when unsealed.

By using the delivery system for a percutaneous absorption drug preparation of the present invention, a liquid drug preparation can be sealed and distributed without leakage or volatilization and diffusion, and can be affixed for administration after simply peeling off the member covering the drug as is the case with typical patches without the need of cumbersome operations when used.

By using the delivery system for a percutaneous absorption drug preparation of the present invention, a constant amount of the liquid drug preparation can be used for transdermally administering the liquid drug preparation to a constant skin area. Contrarily, if a liquid drug preparation were administered as a lotion to the skin, a dose may be unstable, and it may be difficult to keep a dosage constant because the liquid drug applied to the skin can adheres to clothes etc. However, by using the delivery system for a percutaneous absorption drug preparation of the present invention, the troubles as described above can be overcome. As compared to ointment formulations and tapes, liquid drug preparations have good releasability and favorable transdermal absorbability and, therefore, by using the delivery system for a percutaneous absorption drug preparation of the present invention, preparation of patches of liquid drug preparations can be facilitated. As described above, the delivery system for a percutaneous absorption drug preparation of the present invention serves as a new system for liquid drug preparations to enable the expansion of the field in which liquid drug preparations can be utilized and the development of new applications of the liquid drug preparations.

MODES FOR CARRYING OUT THE INVENTION

An embodiment and a method for manufacturing of a delivery system for a percutaneous absorption drug preparation (hereinafter simply referred to as a "system") according to the present invention will now be described with reference to the accompanying drawings.

1-1. Overall Structure

Figure 1:
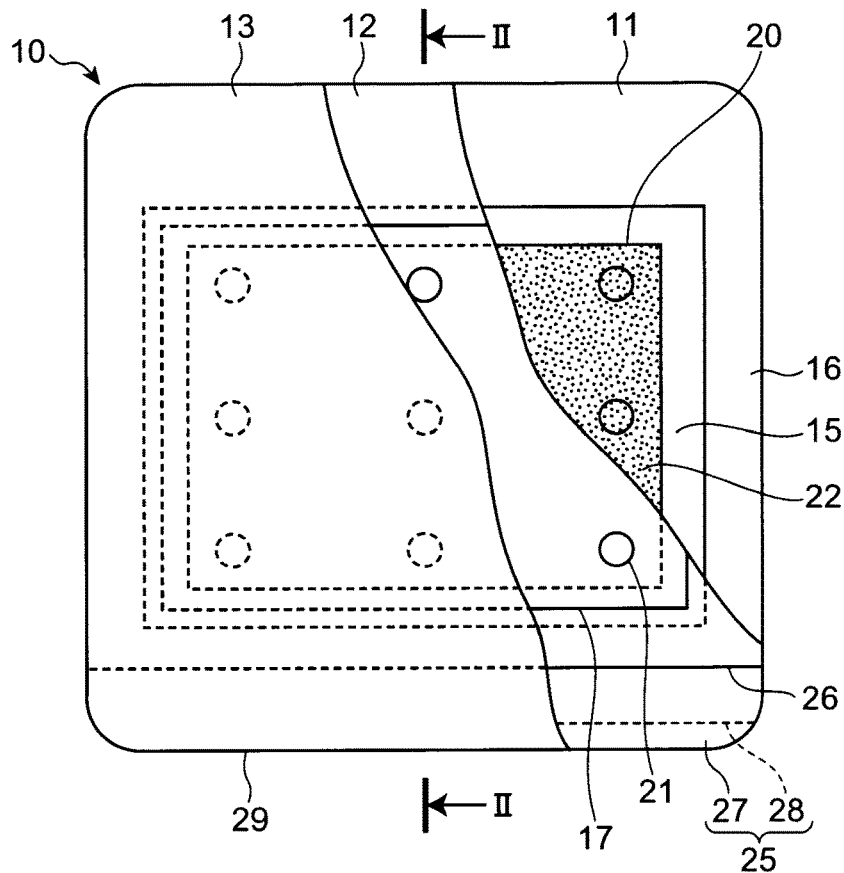
FIG. 1 is a partially cutaway plan view of a delivery system for a percutaneous absorption drug preparation according to the present invention.
Figure 2:
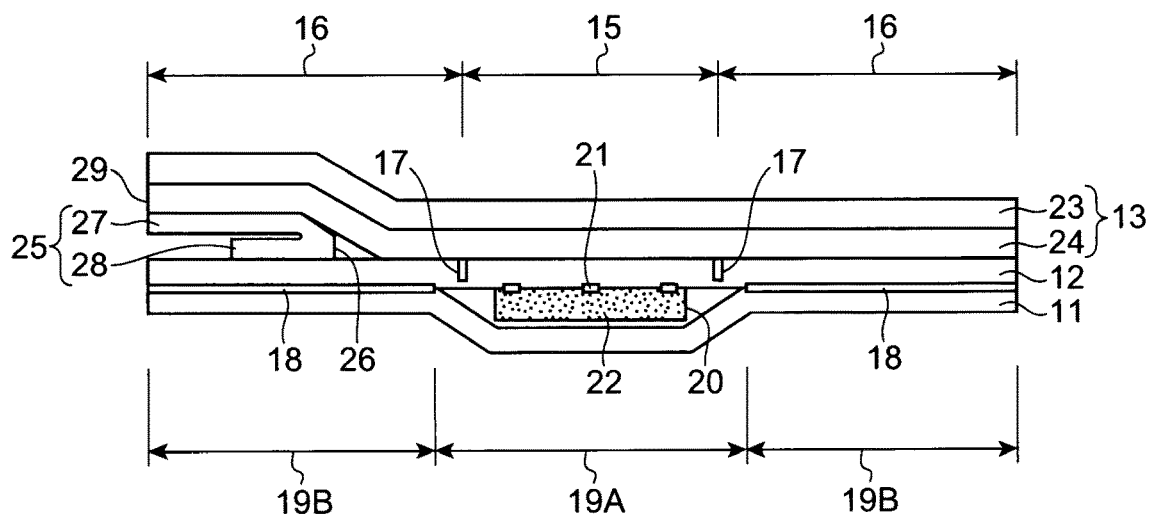
FIG. 2 is a schematic of a cross section taken along a line II-II of the delivery system for a percutaneous absorption drug preparation shown in FIG. 1.

Referring to FIGS. 1 and 2, the system is generally denoted by reference numeral 10 and is constituted by laminating a plurality of sheets or films. In an embodiment, the system 10 has a main part made up of three sheets or films, i.e. a lower-layer cover sheet (first sheet) 11, an intermediate-layer base sheet (second sheet) 12, and an upper-layer backing sheet (third sheet). As shown in FIG. 1, the system 10 has a quadrangular planar shape; however, the shape is not limited thereto and may be circular, elliptical, or other polygonal shapes.

1-2. Cover Sheet (First Sheet) and Base Sheet (Second Sheet)

The lower-layer cover sheet 11 and the intermediate-layer base sheet 12 are preferably formed of a plastic sheet or film or a laminated film made of a solvent-impermeable material and are not particularly limited as long as the sheets are those used with normal heat sealing. Specific examples of the material include polyolefins such as polyethylene and polypropylene, polyesters such as polyethylene terephthalate, polybutylene terephthalate, and polyethylene naphthalate, polyvinyl chloride, polyvinylidene chloride, Polyamide such as nylon-6 and nylon-66, polyimide, ethylene vinyl alcohol, etc., as well as copolymers of these polymers. Preferably, a material used for a sheet or a film made of a plastic-sheet or plastic-film material is a composite material having an aluminum foil disposed between top and bottom plastic layers or a composite material having an aluminum-deposited plastic layer disposed between top and bottom plastic layers.

The base sheet 12 is partitioned into a central inner region 15 and an outer region 16 surrounding the inner region 15. At an annular boundary between the inner region 15 and the outer region 16, a cutting part 17 is formed. The cutting part 17 may be a continuous cut or intermittent perforations. The cutting part 17 may be a so-called full cut reaching from an upper surface to a lower surface of the base sheet 12 or may be a so-called half cut leaving an uncut portion near the upper surface or the lower surface of the base sheet 12. In the case of the full cut, the cutting part is preferably so-called perforations partially leaving an uncut portion. To facilitate avoidance of evaporation and scattering of a solvent of the percutaneous absorption drug preparation contained inside, the cutting part is preferably a so-called half cut. In the shown embodiment, the cutting part 17 is a half cut extending from the upper surface to near the lower surface.

The cover sheet 11 and the base sheet 12 are bonded and sealed by heat sealing 18 to continuously surround the inner region 15 in the outer region 16 such that a non-sealing space (non-sealing region) 19A is formed in the inner region 15 with a seal region 19B formed on the outside thereof. As shown in the figures, the non-sealing space 19A preferably extends beyond the cut part 17 and reaches the outer region 16.

In the non-sealing space 19A, a percutaneous absorption drug preparation carrying member 20 is stored. The percutaneous absorption drug preparation carrying member 20 is fixed to the base sheet 12 by a heat bonding part 21. As shown in the figures, the percutaneous absorption drug preparation carrying member 20 needs not to be bonded on the entire surface and may be spot-welded only in a plurality of small regions. The welding temperature for the fixation is a temperature higher than the melting point of the base sheet 12 and is preferably a temperature lower than the melting point of the percutaneous absorption drug preparation carrying member 20.

1-3. Percutaneous Absorption Drug Preparation Carrying Member

The percutaneous absorption drug preparation-carrying member (hereinafter referred to as "carrying member") 20 is not particularly limited as long as the member is capable of stably containing or retaining a liquid or pasty percutaneous absorption agent 22. For example, cotton fabrics such as absorbent cotton and gauze, nonwoven fabrics, synthetic fiber fabrics such as polyester, polyethylene, and polyvinyl, sponge, and paper are usable. For the sponge, synthetic sponge such as urethane foam or natural sponge is usable. In any case, the carrying member 20 can optimally be selected in accordance with a type of the percutaneous absorption drug preparation carried by the member.

To facilitate welding to the base sheet 12, the carrying member 20 is desirably made of a material not melting at the melting point of the material of the base sheet 12. For example, when polyolefins are used for the base sheet 12, the carrying member 20 is desirably made of a material having the melting point higher than that of the polyolefins used. Preferably, examples can include polyesters having such a melting point.

The percutaneous absorption drug preparation 22 is a liquid, gel-like, or paste-like material containing a medicinal ingredient. For example, the drug preparation can be a liquid having a medicinal ingredient dissolved or dispersed in an inorganic solvent such as water or in an organic solvent. The organic solvent may be any solvents usable as external preparations without particular limitation. An organic ionic liquid is a solvent having a high dissolving power and is also included in these solvents. Furthermore, a mixture thereof is also included. Examples of the organic solvent include fatty acid esters such as isopropyl palmitate, isopropyl myristate, cetyl lactate, diethyl sebacate, hexyl laurate, cetyl isooctanoate, lauryl lactate, and ethyl oleate, glycols such as ethylene glycol, propylene glycol, 1,3-butylene glycol, polyethylene glycol, polypropylene glycol, and glycerin, and alcohols such as ethanol, propanol, isopropanol, and butanol.

Examples of the organic ionic liquid include a Brønsted type salt composed of a fatty acid and an organic amine compound which is liquid at room temperature. The fatty acid and the organic amine compound are not particularly limited as long as these are usable as a patch. Examples include fatty acids such as levulinic acid, octanoic acid, decanoic acid, oleic acid, stearic acid, and isostearic acid, and lower alkylamines such as diethanolamine, diisopropanolamine, triethanolamine, and triisopropanolamine.

A percutaneous absorption promoter may be added to the percutaneous absorption drug preparation. Examples of the percutaneous absorption promoter include higher alcohols such as cetanol, stearyl alcohol, lauryl alcohol, cetostearyl alcohol, myristyl alcohol, and oleyl alcohol, menthol, and limonene. Furthermore, for example, one or more selected from ester solvents such as isopropyl myristate, isopropyl palmitate, diethyl sebacate, and propylene carbonate, and N-methyl-2-pyrrolidone are usable. A surfactant can also be used, and examples of the surfactant include a nonionic surfactant, an anionic surfactant, a cationic surfactant, and an amphoteric surfactant. Examples of the nonionic surfactant include sorbitan monolaurate, sorbitan monopalmitate, sorbitan sesquioleate, glycerin monostearate, decaglyceryl monolaurate, hexaglycerin polyricinoleate, polyoxyethylene (9) lauryl ether, polyoxyethylene (2) lauryl ether, polyoxyethylene (4,2) lauryl ether, polyoxyethylene (5) nonylphenyl ether, polyoxyethylene (7,5) nonylphenyl ether, polyoxyethylene (10) nonylphenyl ether, polyoxyethylene (3) octylphenyl ether, polyoxyethylene (10) octylphenyl ether, polyoxyethylene (10) oleylamine, polyoxy (5) oleylamine, polyoxy (5) oleic amide, Polyoxyethylene (2) monolaurate, monoglyceride stearate, polyoxyethylene castor oil (hardened castor oil), etc.

Examples of the anionic surfactant include sodium lauryl sulfate, potassium lauryl sulfate, triethanolamine lauryl sulfate, sodium cetyl sulfate, sodium lauroyl sarcosinate, sodium di-2-ethylhexyl sulfosuccinate, sodium polyoxyethylene (10) lauryl ether phosphate, sodium polyoxyethylene (4) lauryl ether phosphate, sodium polyoxyethylene (5) cetyl ether phosphate, sodium polyoxyethylene (6) oleyl ether phosphate, etc.

Examples of the cationic surfactant include stearyl trimethyl ammonium chloride, distearyl dimethyl ammonium chloride, benzalkonium chloride, stearyl dimethyl benzyl ammonium chloride, etc.

Examples of the amphoteric surfactant include phosphatidylcholine, lauryldimethylaminoacetic acid betaine, 2-alkyl-N-carboxymethyl-N-hydroxyethylimidazolinium betaine, etc. For another example, lauroyl diethanol amide can also be used.

The percutaneous absorption drug preparation can be a percutaneous absorption liquid drug having a medicinal ingredient dissolved or dispersed in propylene glycol in the presence of phosphatidylcholine.

The "medicinal ingredient" is not particularly limited as long as the ingredient is usable as a percutaneous absorption drug preparation, and examples thereof include nonsteroidal anti-inflammatory drugs (NSAIDs) such as indomethacin, flurbiprofen, ketoprofen, and diclofenac, local anesthetics such as lidocaine and dibucaine, tramadol, eperisone, ramelteon, donepezil, escitalopram, galantamine, ramelteon, morphine, oxycodone, paroxetine, ropinirole, pergolide, ondansetron, raloxifene, rotigotine, aripiprazole, fentanyl, apomorphine, memantine, amantadine, tulobuterol, tolbutamide, glibenclamide, oxybutynin, neostigmine, nicardipine, dopamine, etc. Furthermore, a combination of these medicinal ingredients can be used. A medicinal ingredient converted to an ionic liquid due to a combination of an acid and a base is also usable. Preferable examples include a combination between the NSAID described above serving as an acid and the local anesthetic serving as a base.

The "solvent" refers to an aqueous solution for dissolving the medicinal ingredient or the organic solvent described above. The organic solvent further refers to those containing the percutaneous absorption promoter described above. Therefore, the organic solvent may be any solvents usable for a patch for percutaneous absorption without particular limitation. An organic ionic liquid is a solvent having a high dissolving power and is also included in these solvents. Furthermore, a mixture thereof is also included. Therefore, the percutaneous absorption drug preparations having the medicinal ingredients dissolved in the organic ionic liquid and the organic solvent are also usable.

1-4. Backing Sheet (Third Sheet)

The backing sheet 13 has a base material layer 23 and an adhesive layer 24 disposed on the lower surface of the base material layer 23. The base material layer 23 is made up of a nonwoven fabric, a woven fabric, a synthetic resin sheet, or a composite thereof. Examples of these materials of the backing sheet include polyethylene, polypropylene, polycarbonate, polyesters, polyamide, polyvinyl chloride, cotton, urethane, etc., and further include composites thereof.

The adhesive layer 24 is made up of an adhesive material capable of exerting a required adhesive force for the upper surface of the base sheet 12. When the cutting part 17 of the base sheet 12 is the full cut, an adhesive is used that can prevent the percutaneous absorption drug preparation stored in the non-sealing space 19A between the cover sheet 11 and the base sheet 12 from passing and leaking through the interface between the adhesive layer 24 and the base sheet 12 to the outside. Specifically, acrylic, synthetic-rubber-based, and natural-rubber-based adhesives etc. can appropriately be selected and used, and preferable examples include acrylic adhesives mainly composed of a copolymer of an acrylic monomer such as 2-ethylhexyl acrylate, butyl acrylate, ethyl acrylate, and methyl methacrylate, and synthetic-rubber-based adhesives such as tackifiers including a styrene-isoprene-styrene copolymer (SIS) and a terpene resin. To improve liquid resistance, trimellitate ester plasticizer or polyester plasticizer can be used together as a plasticizer.

1-5. Release Sheet (Fourth Sheet)

As shown in FIGS. 1 and 2, preferably, a release sheet (fourth sheet) 25 is disposed between the base sheet 12 and the backing sheet 13 along one edge of the system 10. As shown in FIG. 2, the release sheet 25 is made of a band-like sheet or film and may be folded at a fold line 26 in the longitudinal direction. For example, the sheet may be made up of two seat portions 27, 28 with the fold line 26 interposed therebetween. As shown in the figures, the width of one of the two seat portions 27, 28 is larger than the width of the other. The release sheet 25 folded in this way is disposed between the base sheet 12 and the backing sheet 13 with a longitudinal end edge portion of a wide sheet portion 27 made coincident with an edge 29 of the backing sheet 13. Therefore, the release sheet 25 has the upper surface of the wide sheet portion 27 affixed to and retained by the adhesive layer 24 of the backing sheet 13. The lower surface of the narrow sheet portion 28 on the other side is in contact with the base sheet 12 without being affixed thereto.

Although not particularly limited, the release sheet 25 can be made up of a sheet of polyethylenes, polypropylenes, polyesters, etc. These sheets can have a sheet surface silicon-processed so as to facilitate peeling from a plaster.

2. Method for Manufacturing

A method for manufacturing a system having the configuration described above will be described with reference to FIG. 3. Although FIG. 2 shows the cover sheet 11 on the lower side and the backing sheet 13 on the upper side in consideration of the usage state of the system, the positions are inverted from FIG. 2 in a manufacturing process described below, so that the backing sheet and the cover sheet 11 are positioned on the lower side and the upper side, respectively.

The manufacturing process includes the following steps 1 to 10. Each of the steps will hereinafter be described.

Step 1: Supply of Base Sheet

Figure 3:
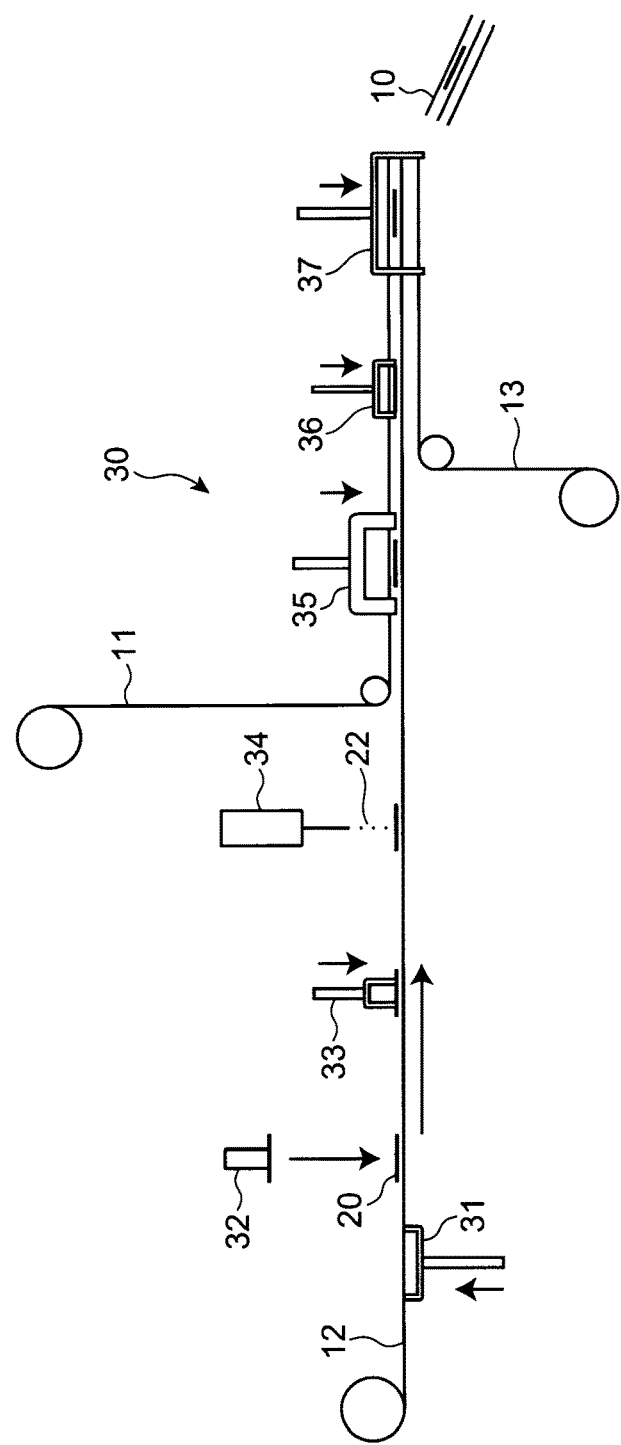
FIG. 3 is a diagram of a manufacturing process of the delivery system for a percutaneous absorption drug preparation shown in FIG. 1.

In a manufacturing process 30 shown in FIG. 3, the base sheet 12 is continuously supplied from the left side to the right side of FIG. 3.

Step 2: Formation of Cutting Part

A cutter 31 is brought into contact with the lower surface of the base sheet 12 to form the cutting part 17. Although not shown, a support table is disposed on the side opposite to the cutter 31 across the base sheet 12, and the cutting part 17 is formed in the base sheet 12 sandwiched by the cutter 31 and the support table. As described above, the type of the cutter 31 is selected depending on the type of the cutting part 17 (a continuous cut, perforations, a full cut, or a half cut).

Step 3: Supply of Carrying Member

A carrying member supplying device 32 places the carrying member 20 on the upper surface of the base sheet 12.

Step 4: Fixation of Carrying Member

The carrying member 20 and the base sheet 12 are welded at a plurality of positions by, for example, an ultrasonic spot welding machine 33 to form the heat bonding part 21.

Step 5: Supply of Drug Preparation

The percutaneous absorption drug preparation 22 is supplied from a drug preparation supplying device 34 to the carrying member 20.

Step 6: Supply of Cover Sheet

The cover sheet 11 is supplied and overlaid on the base sheet and the carrying member.

Step 7: Heat Sealing

A heat sealer 35 is used for the heat sealing 18 of the base sheet 12 and the outer region 16 of the cover sheet 11 and an outside region thereof. The inner region 15 having the carrying member 20 located therein is not heat-sealed.

Step 8: Supply of Backing Sheet

The backing sheet 13 is supplied and overlaid on the base sheet 12.

Step 9: Laminate

The base sheet 12 with the backing sheet 13 overlaid thereon is pressed from above and below by a laminating device 36 to cause the backing sheet 13 to adhere to the base sheet 12 through the adhesive layer 24 of the backing sheet 13.

Step 10: Punching

A laminated body made up of a plurality of sheets laminated as described above is punched out by a punching cutter 37 having a blade along the contour of the system 10.

Although not particularly mentioned in the above description of the process, the double-folded release sheet 25 may be attached to the edge of the backing sheet 13 in advance to supply at Step 8 the backing sheet 13 having the release sheet 25 affixed in this way, or a step of supplying the double-folded release sheet 25 may be provided before Step 8.

In the above description, the step of forming the cutting part 17 in the base sheet 12 is provided immediately before the carrying member supply step 3; however, the cutting part formation step may be provided at any time point before the backing sheet supply step.

3. Use

The use of the system 10 manufactured as above will be described.

Figure 4A:
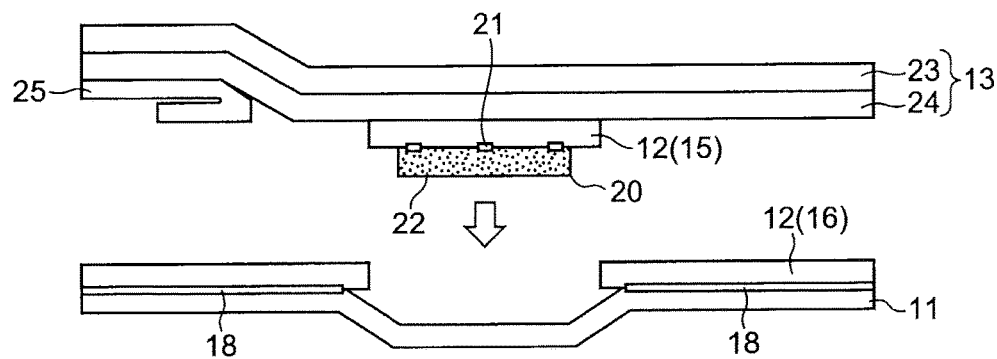
FIGS. 4A, 4B and 4C are a schematic of a usage state of the delivery system for a percutaneous absorption drug preparation shown in FIG. 1.
Figure 4B:
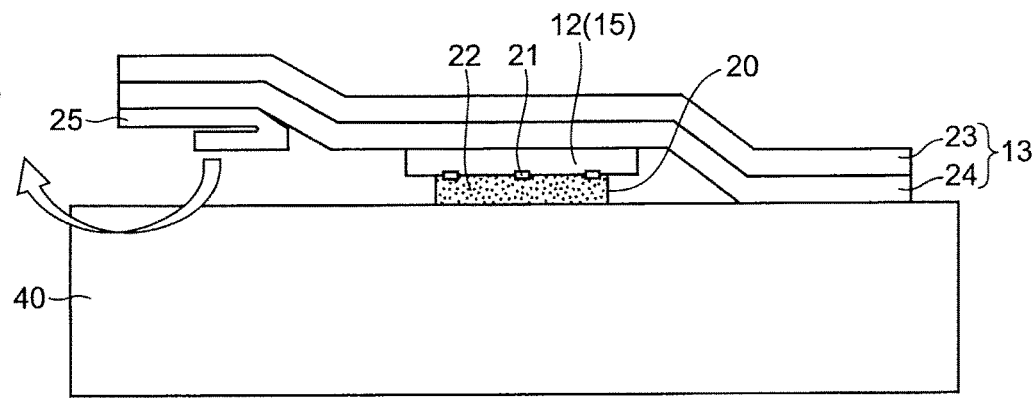
Figure 4C:
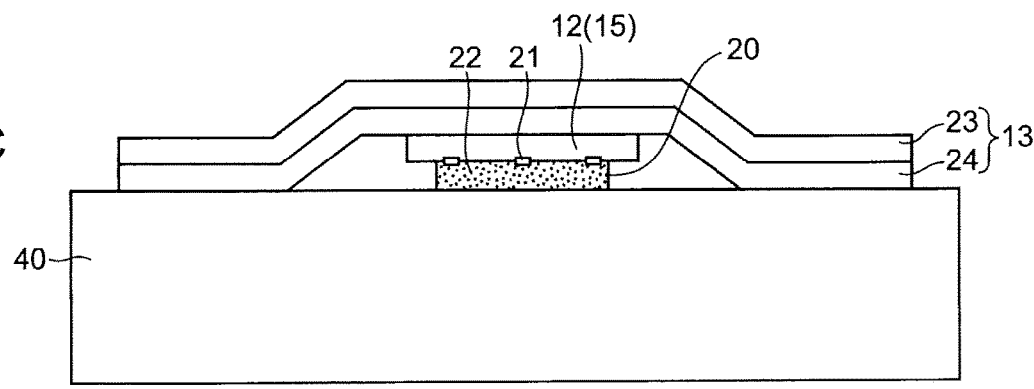

As shown in FIGS. 4A, 4B and 4C, when used, the base sheet 12 and the cover sheet 11 are held by the adhesion portion thereof contacting with the release sheet 25 and are peeled off from the backing sheet 13. In this regard, as shown in FIG. 4A, the base sheet 12 has the cutting part 17 formed between the inner region 15 and the outer region 16 thereof. Therefore, the inner region 15 of the base sheet 12 remains on the backing sheet 13 because of the adhesive layer 24 without being peeled off from the backing sheet 13. The carrying member 20 fixed to the inner region 15 of the base sheet 12 also remains on the backing sheet 13 along with the inner region 15.

Subsequently, as shown in FIG. 4B, the system 10 with the cover sheet 11 and the outer region 16 of the base sheet 12 removed is affixed such that the adhesive layer 24 is placed on a skin 40. Lastly, as shown in FIG. 4C, the release sheet 25 is peeled off and the whole of the adhesive layer 24 is affixed to the skin 40.

As described above, according to the system 10 of the embodiment, the drug preparation carrying member 20 is retained on the backing sheet 13 after the cover sheet 11 and the outer region 16 of the base sheet 12 are peeled off from the system 10, and therefore can directly be affixed to the skin 40 along with the backing sheet 13. Additionally, since it is not necessary to perform an operation such as adjusting the position of the carrying member 20 with respect to the backing sheet 13, the drug preparation does not adhere to the user's finger.

EXPLANATIONS OF LETTERS OR NUMERALS 10 delivery system for percutaneous absorption drug preparation
11 cover sheet (first sheet)
12 base sheet (second sheet)
13 backing sheet (third sheet)
15 inner region
16 outer region
17 cutting part
18 heat sealing
19A non-sealing space (non-sealing region)
19B sealing region
20 percutaneous absorption drug preparation carrying member
21 heat bonding part
22 percutaneous absorption drug preparation
23 base material layer
24 adhesive layer
25 release sheet (fourth sheet)
26 fold line
27 wide sheet portion
28 narrow sheet portion
29 edge of backing sheet
30 manufacturing process
31 cutter
32 carrying member supplying device
33 ultrasonic spot welding machine
34 drug preparation supplying device
35 heat sealer
36 laminating device
37 punching cutter
40 skin

The invention claimed is:

1. A delivery system for a percutaneous absorption drug preparation comprising:
(a) a solvent-impermeable first sheet;
(b) a solvent-impermeable second sheet, the second sheet being partitioned by making a cutting part in the second sheet into a central inner region and an outer region surrounding the inner region, the second sheet being bonded and sealed to an upper surface of the first sheet by heat sealing to form a non-sealing region and a sealing region surrounding the non-seal region such that a non-sealing space is formed between the first sheet and the second sheet, the cutting part annularly extending along an outer circumferential edge of the non-sealing region;
(c) a percutaneous absorption drug preparation carrying member disposed in the non-sealing space between the first sheet and the second sheet in the non-sealing region and fixed to the inner region of the second sheet inside the cutting part; and
(d) an adhesive third sheet affixed in a peelable manner to an upper surface of the second sheet.

2. The delivery system for a percutaneous absorption drug preparation according to claim 1, wherein
the third sheet has a support layer and an adhesive layer disposed on a surface of the support layer facing the second sheet, and wherein
the adhesive layer is affixed in a peelable manner to the second sheet.

3. The delivery system for a percutaneous absorption drug preparation according to claim 2, comprising a fourth sheet disposed between the second sheet and the third sheet along at least a portion of an outer circumferential edge of the third sheet and affixed in a peelable manner to the adhesive layer of the third sheet.

4. The delivery system for a percutaneous absorption drug preparation according to claim 1, wherein the percutaneous absorption drug preparation carrying member is fixed to the second sheet by spot welding at a plurality of positions.

5. A delivery system for a percutaneous absorption drug preparation comprising:
(a) a backing sheet having a base material layer and an adhesive layer disposed on a lower surface of the base material layer;
(b) a solvent-impermeable base sheet affixed in a peelable manner to a lower surface of the adhesive layer and having an annular cutting part, an inner region located inside the annular cutting part, and an outer region located outside the annular cutting part;
(c) a percutaneous absorption drug preparation carrying member fixed to the base sheet in the inner region of the base sheet; and
(d) a solvent-impermeable cover sheet disposed on a lower surface of the base sheet to cover at least the inner region, the cover sheet being fixed to the base sheet in the outer region of the base sheet to continuously seal the circumference of the inner region,
(e) the device allowing the outer region of the base sheet to be peeled off along with the cover sheet fixed to the outer region while leaving the inner region of the base sheet on the backing sheet along with the percutaneous absorption drug preparation carrying member,
wherein the second sheet is partitioned by making the cutting part in the second sheet into the central inner region and the outer region surrounding the inner region.

6. The delivery system for a percutaneous absorption drug preparation according to claim 5, comprising a release sheet disposed between the base sheet and the backing sheet along at least a portion of an outer circumferential edge of the backing sheet and affixed in a peelable manner to the adhesive layer of the backing sheet.

7. The delivery system for a percutaneous absorption drug preparation according to claim 5, wherein the percutaneous absorption drug preparation carrying member is fixed to the base sheet by spot welding at a plurality of positions.

8. A method for manufacturing a delivery system for a percutaneous absorption drug preparation comprising:
a step 1 of supplying a solvent-impermeable base sheet including an outer region and an inner region surrounded by the outer region;
a step 2 of forming an annular cutting part in the base sheet along an outer circumferential edge of the inner region to partition the base sheet into the inner region and the outer region;
a step 3 of disposing a percutaneous absorption drug preparation carrying member in the inner region on a lower surface of the base sheet;
a step 4 of fixing the percutaneous absorption drug preparation carrying member to the base sheet;

a step 5 of allowing the percutaneous absorption drug preparation carrying member to carry a drug preparation;

a step 6 of disposing a solvent-impermeable cover sheet on the lower surface of the base sheet to cover the percutaneous absorption drug preparation carrying member carrying the drug preparation;

a step 7 of fixing the cover sheet to the base sheet and sealing between the base sheet and the cover sheet in the outer region; and a step 8 of affixing a backing sheet in a peelable manner to an upper surface of the base sheet.

\* \* \* \* \*